(12) United States Patent
Bol et al.

(10) Patent No.: US 7,274,026 B2
(45) Date of Patent: Sep. 25, 2007

(54) APPARATUS AND PROCESS FOR IRRADIATING PRODUCT PALLETS

(75) Inventors: Jean-Louis Bol, Genappe (BE); Benoit Mullier, Corroy-le-Chateau (BE); Fréderic Stichelbaut, Mazy (BE); Glenn Nelson, Placerville, CA (US)

(73) Assignee: Ion Beam Application S.A., Louvain-la-Neuve (BE)

( * ) Notice: Subject to any disclaimer, the term of this patent is extended or adjusted under 35 U.S.C. 154(b) by 0 days.

(21) Appl. No.: 10/505,036

(22) PCT Filed: Feb. 13, 2003

(86) PCT No.: PCT/BE03/00024
§ 371 (c)(1),
(2), (4) Date: Mar. 25, 2005

(87) PCT Pub. No.: WO03/072148
PCT Pub. Date: Sep. 4, 2003

(65) Prior Publication Data
US 2005/0167613 A1 Aug. 4, 2005

(30) Foreign Application Priority Data
Feb. 28, 2002 (EP) .................................. 02447030

(51) Int. Cl.
*G01N 21/00* (2006.01)

(52) U.S. Cl. ............................ 250/453.11; 250/454.11; 250/455.11

(58) Field of Classification Search ........... 250/455.11, 250/453.11, 454.11
See application file for complete search history.

(56) References Cited

U.S. PATENT DOCUMENTS

| 3,686,502 | A | * | 8/1972 | Sieber ...................... 250/492.1 |
| 4,018,348 | A | | 4/1977 | Bosshard |
| 5,740,221 | A | | 4/1998 | Norman et al. |
| 6,690,020 | B2 | * | 2/2004 | Loda ...................... 250/455.11 |

FOREIGN PATENT DOCUMENTS

JP     2001249200      9/2001

OTHER PUBLICATIONS

Abs et al. "X-ray Pasteurization of Food with the next generation Rhodotrons" Electralis 2001—The Campus: Research Project Submission *Ion Beam Applications, Louvain-la-Neuve*, Belgium. XP-002199149.

* cited by examiner

*Primary Examiner*—David Vanore
(74) *Attorney, Agent, or Firm*—Fitch, Even, Tabin & Flannery

(57) ABSTRACT

The present invention is related to an apparatus for irradiating products conveyed on a pallet, comprising a beam source (3) for producing a radiation beam, a shielding wall (4) encompassing an irradiation chamber (2) and a revolving cylindrical door (6) having a recess (8) for holding said pallet, for bringing said pallet in and out of the irradiation chamber (2) wherein said high-energy radiation beam is directed towards a lateral side of said revolving door (6), for irradiating said pallet in said recess (8), or brought before said recess (8).

The present invention is also related to a process wherein a product pallet is brought into an irradiation chamber (2) through a revolving cylindrical door (6) having a recess (8), and irradiated while in said recess (8) or in front of said recess (8).

11 Claims, 8 Drawing Sheets

APPARATUS AND PROCESS FOR IRRADIATING PRODUCT PALLETS

FIELD OF THE INVENTION

The present invention is related to an apparatus for irradiating products conveyed on pallets or carriers with a radiation beam.

A possible application of such apparatus and process is the sterilisation of products and pasteurisation of food products.

STATE OF THE ART

Irradiation systems have widely been used for sterilising a great variety of products such as medical devices, food, food utensils or cosmetics by means of a high-energy ionising radiation source. Traditionally, the radiation source was a radioactive element producing gamma rays, such as Cobalt 60. For reasons of safety, i.a. in the disposal of waste, these systems are now replaced by systems relying on the use of an electron accelerator for producing a high-energy electron beam. This high-energy electron beam is either directed immediately to the product to be treated, or passed through a foil made of a high Z material, for producing X-rays.

Typically, in these irradiation systems, products are loaded either on pallets or on unique carrier trays and maintained in a store before the irradiation chamber before being conveyed past the radiation source for irradiation. A second pass of the pallets or carriers may then be planned in order to expose another side to the radiation source.

The irradiation chamber is separated from the environment by a shielding wall made of heavy material such as concrete. It must be possible to bring products in and out of the irradiation chamber without allowing radiation to leave the irradiation chamber.

One solution known in the art is to use an angled passageway, or maze, for bringing the products into the irradiation chamber. Preferably, a dual maze, having an entry path and an exit path, is used, in order to avoid contact of the entering untreated products with the already treated products. Such systems are known e.g. from Document "Electron Beam Sterilization Technology" (Radiat. Phys. Chem. Vol. 14, pp.403-414 James H. Bly) describing a typical facility for e-beam sterilization (see FIG. 6 of said document). Another example of such an installation is known from U.S. Pat. No. 6,127,687. In this document, the irradiation chamber comprises in addition a reroute conveyor and a mechanism for reorienting the carriers, allowing performing double side irradiation of the product without leaving the irradiation chamber.

Another solution known in the art is to use a rotary lock. According to this principle, a cylindrical aperture is left in the shielding, and a rotating cylindrical door, having at least one recess for holding a pallet or carrier is provided for bringing pallets or carriers in and out of the irradiation chamber. The rotating cylindrical door is made of a radiation absorbing material such as concrete. The size and material of the cylindrical door are chosen such that, for any position of the rotating door, a sufficient amount of shielding material is provided between the irradiation chamber and the outside of it. Various embodiments and improvements of this principle are known from U.S. Pat. No. 3,686,502, U.S. Pat. No. 4,018,348, and U.S. Pat. No. 4,281,954. In all these embodiments, the Cobalt 60 source is located centrally in the irradiation chamber, irradiating in all directions, and a conveyor system is provided inside the irradiation chamber for exposing two or more sides of the product to the source.

Another apparatus known in the art from U.S. Pat. No. 5,554,856 comprises a transporter in the shape of a disk. Products to be irradiated are loaded onto said disk, or in a recess provided in said disk. The disk is then rotated around a vertical axis, for bringing the product inside an irradiation cell in order to be irradiated from above by an electron beam.

Concrete shielding walls having thicknesses of 2 m or more are commonly used in the industry. Such a shielding is a significant part of the cost of an irradiation apparatus.

When the maze solution is used for bringing products in and out of the irradiation chamber, the maze itself adds to the size and cost of shielding. The conveyor system for transporting the pallets or carriers across the maze, with many angles, is not only part of the cost of the installation, but also of the time necessary to process products. Moreover, in the maze solution, in order to permanently have a product pallet ready for passing the beam, there must be a number of product pallets in a waiting queue in the entry path of the maze. Therefore, the time between unload from a truck of an untreated product pallet to reload on a truck of a treated product pallet cannot be reduced below some limit without impairing throughput of the installation.

The known rotary lock systems have a complex conveyor system inside the irradiation chamber. The irradiation chamber is therefore very large. Moreover, the maintenance of this mechanical device in a high radiation area requires stringent safety measures.

The known rotary disk system allows performing electron-beam irradiation of small packages from above, but is not capable of treating larger packages. Moreover, irradiation can only be performed from one side, i.e. from above. A uniform irradiation dose cannot be achieved in these conditions.

Document U.S. Pat. No. 5,740,221 is related to X-ray inspection of products, in particular (but not limited to) air bag inflators. X-rays for inspection systems are traditionally low energy x-rays, in the range of 50 to 100 Kev. The shielding requirements are much lower than the shielding requirements in irradiation systems, where either electron beams or x-rays are used in the range of 5 MeV. Being an inspection system, the disclosed device requires the presence of a visual imager inside the chamber. The system of U.S. Pat. No. 5,740,221 involves an irradiation chamber, comprising on opposite sides two entry/exit assemblies, which each comprise a revolving door. The doors are placed over a conveyer belt, and the products are not actually transported (rotated) by the rotation of the door. The doors are rotated with respect to the products which are underneath them. Furthermore, the radiation source does not direct a beam to the lateral side of the product, but to the bottom side In the document entitled 'X-ray pasteurization of food with next generation of Rhodotrons', by Abs et al., the Rhodotron electron accelerator is described. The document mentions a conveyor system (scan horn). However, the concept of a revolving door cannot be derived from this document.

In JP2001249200 (Patent Abstract), an irradiating device is described capable of uniformly irradiating the whole face of an object, by rotating the object in the vertical and horizontal plane.

Document U.S. Pat. No. 4,018,348 is related to an irradiation system using a radioactive source such as Cobalt60. Such a source is isotropic, i.e. irradiates equally in all directions of space, so it cannot be specifically directed to one side of a product.

AIMS OF THE INVENTION

The present invention aims to provide an apparatus and process for irradiating products, which do not present the drawbacks of the apparatuses and processes of the state of the art mentioned here above.

More precisely, the present invention aims to provide an irradiation apparatus and process where the shielding size is minimized and which is capable of achieving a high throughput.

SUMMARY OF THE INVENTION

The present invention is related to an apparatus for irradiating products conveyed on a pallet comprising:
a beam source for producing a high-energy radiation beam;
a shielding wall encompassing an irradiation chamber;
a revolving cylindrical door having at least one recess for holding said pallet, for bringing said pallet in and out of the irradiation chamber;
means for directing said high-energy radiation beam towards a lateral side of said revolving door.

Preferably, the apparatus comprises means for rotating said pallet during irradiation, in order to achieve a uniform irradiation dose. Said means may be a turntable, located in one embodiment of the invention, inside said recess, or in another embodiment of the invention, in the irradiation chamber, in the vicinity of the revolving door.

Advantageously, the apparatus comprises two or more cylindrical doors, means for directing said high-energy radiation beam towards a lateral side of each revolving door, and means for switching said high energy radiation beam to each of said revolving doors. The throughput of this apparatus may be increased by performing irradiation of the product placed in or coming from one revolving door, while simultaneously bringing a product pallet in or out of the irradiation chamber with an other revolving door.

In another aspect of the invention, a cylindrical door comprises two or more recesses. This also allows a better throughput by performing irradiation of the product placed in or coming from one recess, or bringing said product pallet in or out of said recess, while simultaneously bringing a product pallet in or out of an other recess of said revolving door.

The present invention is also related to a process for irradiating products conveyed on a pallet characterized in that it comprises the steps of:
revolving a cylindrical door for bringing a recess in said door to the outside of an irradiation chamber;
transferring said pallet into said recess;
revolving said cylindrical door for bringing said recess to the inside of said irradiation chamber;
irradiating said product by directing a beam of high-energy radiation to it's lateral side;
revolving said cylindrical door for bringing said recess to the outside of said irradiation chamber;
transferring said pallet out of said recess by a horizontal movement.

In one embodiment of the invention, the process further comprises the step of bringing said pallet out of said recess, in the irradiation chamber, before irradiating it.

In another embodiment of the invention, the process further comprises the step of rotating said pallet during the irradiation.

Advantageously, a pallet is transferred in and/or out of a recess in a cylindrical door, while another pallet is being irradiated from another recess in said cylindrical door, thereby increasing throughput.

In another aspect of the process of the invention, a pallet is being irradiated from a recess in a cylindrical door while another pallet is being transferred in and/or out of a recess in another cylindrical door and/or said other cylindrical door is being revolved. This again allows increasing throughput of the installation.

SHORT DESCRIPTION OF THE DRAWINGS

DESCRIPTION OF A PREFERRED EMBODIMENT OF THE INVENTION

Figure 1:
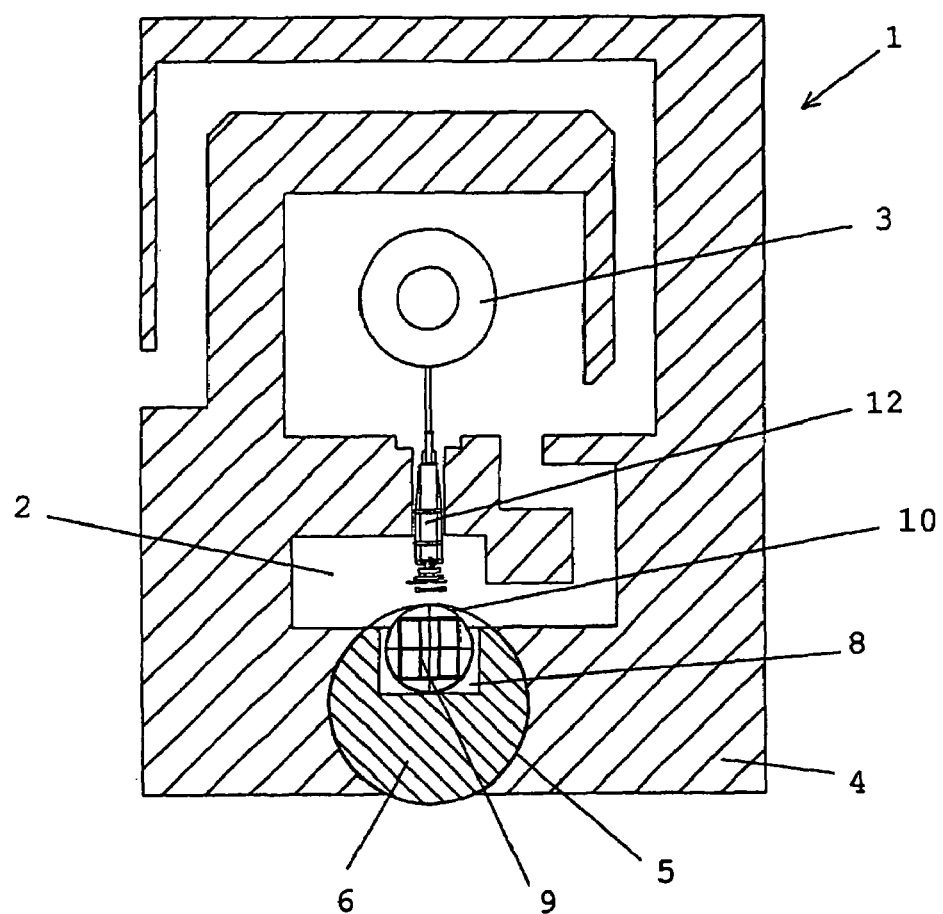
FIG. 1 represents a general top view of the irradiation apparatus according to a first embodiment of the present invention, with a turntable located within the revolving door recess.
Figure 2:
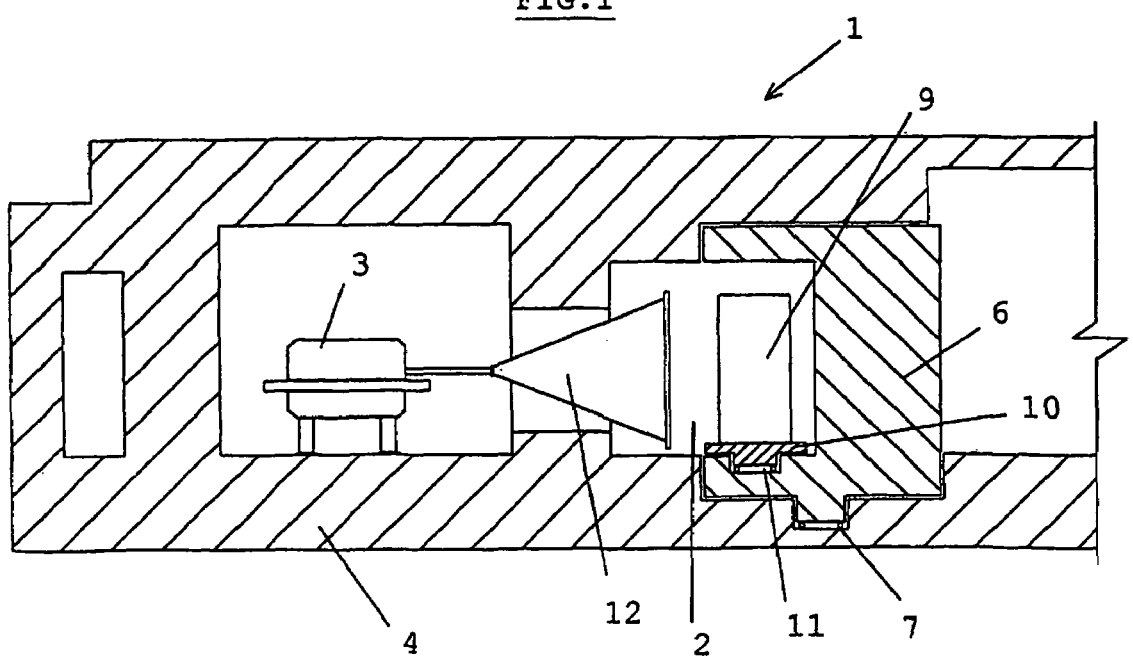
FIG. 2 represents a vertical sectional view along the line II-II of FIG. 1.

A preferred first embodiment of the present invention is illustrated on FIGS. 1 and 2.

The apparatus 1 comprises an irradiation chamber 2 where irradiation takes place and a beam source 3 producing a beam of accelerated particles. The beam source may be a Rhodotron, as shown, a Dynamitron, or any type of charged particle accelerator. The irradiation chamber 2 and the beam source 3 are surrounded by a shielding wall 4. The shielding wall 4 may be made of concrete, or any radiation absorbing material such as iron, lead, or combinations thereof. The shielding wall 4 comprises a cylindrical opening 5. Fitted in said cylindrical opening 5, there is a cylindrical revolving door 6. This revolving door 6 rests on a ball bearing 7 and can be revolved around the cylinder axis by a motor (not shown). The revolving door is made of radiation shielding material. A recess 8 is made in the revolving door. The shape and size of said recess 8 is such that a product pallet or carrier 9 can be brought into and out of said recess 8 by a horizontal translation movement. In the first embodiment of the invention, shown in FIG. 1, a turntable 10 is installed in the recess 8, on a ball bearing 11, in order to rotate the product pallet around a vertical axis, in said recess 8. In this embodiment, the size of the recess 8 must be such that rotation of a product pallet 9 is allowed. A scan horn 12 is used in combination with a set of deflecting magnets for directing the beam at the lateral side of the revolving door 6 and thus along the whole height of the product pallet 9. The rotation of the product pallet 9 during the irradiation allows to obtain an even irradiation dose throughout the product pallet 9. The exit window of the scan horn 12 may be a thin foil in which case irradiation is by the electron beam directly. Preferably, a so-called x-ray conversion window, made of a foil of high Z material, may be used for converting the radiation from electron beam to X-rays. The X-rays having a much better penetration capacity in matter, a product pallet of higher density material can be irradiated efficiently.

Figure 3:
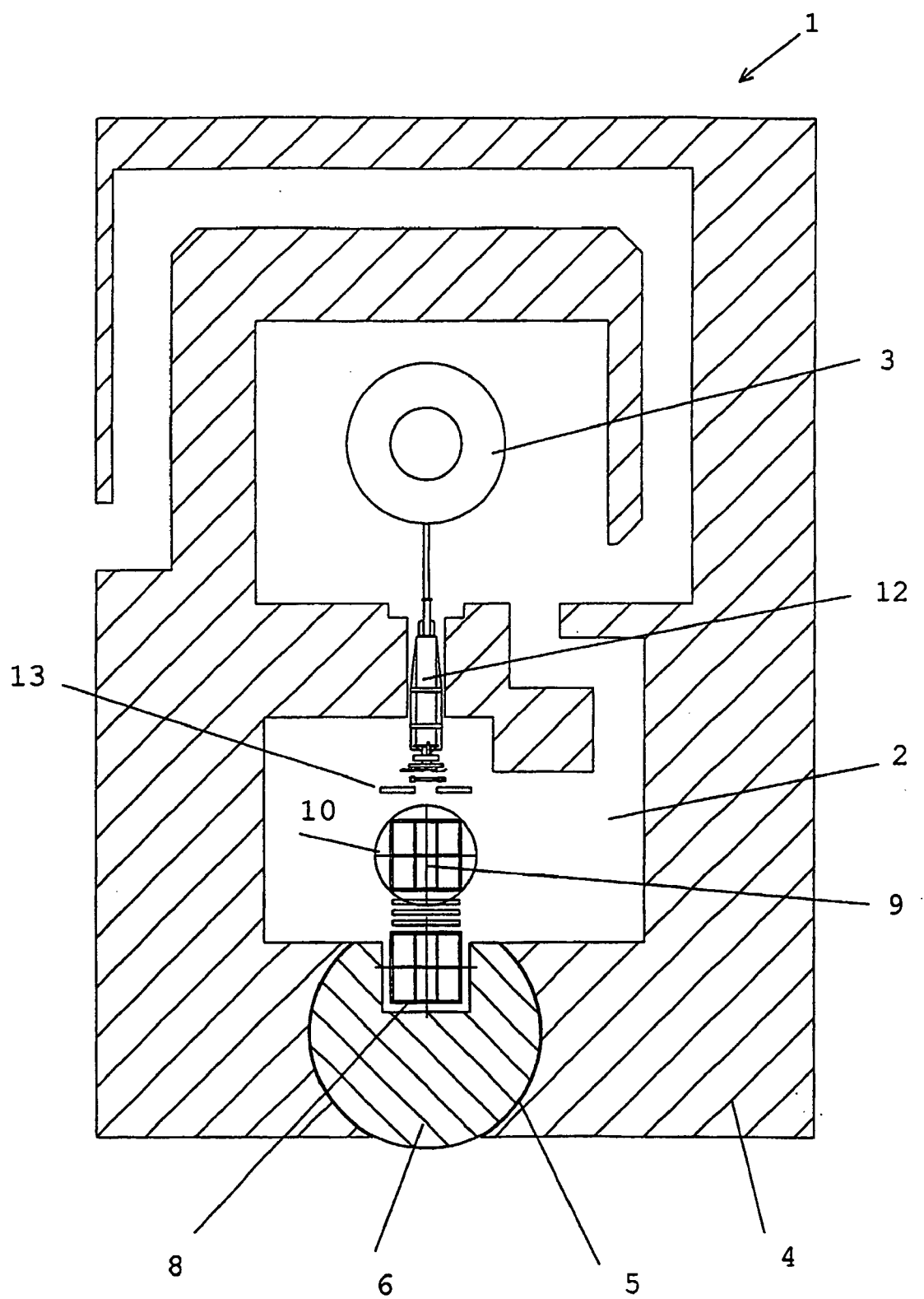
FIG. 3 represents a general top view of the irradiation apparatus according to a second embodiment of the present invention, with a turntable located inside the irradiation chamber.

A second embodiment of the present invention is illustrated on FIG. 3. Same items have same numbers. A difference with respect to the first embodiment is that the turntable 10 is located in the irradiation chamber 2 instead of inside the recess 8. A conveyor means allows transport of a product pallet 9 from the recess 8 onto the turntable 10. Once the product pallet 9 is on the turntable 10, irradiation starts, while the product pallet 9 is rotated. The width of the beam may be controlled by the use of a variable-width collimator 13. In this embodiment, the construction of the revolving door is simple, because it does not comprise a turntable 10. On the other hand, the irradiation chamber 2 is slightly larger, and an additional time is required for transporting the product pallet 9 in and out of the irradiation chamber 2.

Figure 4:
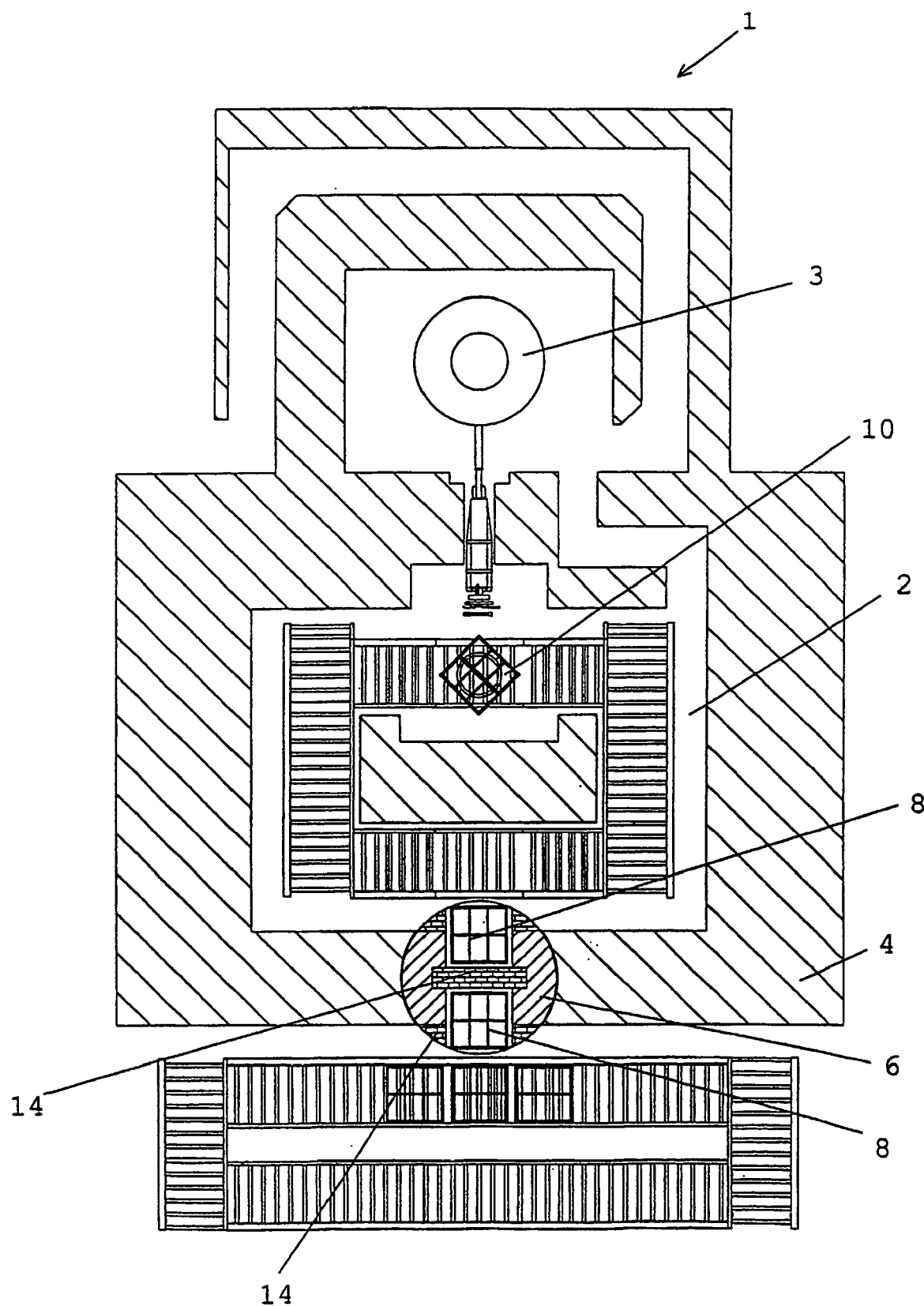
FIG. 4 represents a general top view of the irradiation apparatus according to a third embodiment of the present invention, with a short conveyor loop inside the irradiation chamber.

FIG. 4 shows a third embodiment of the invention. A short loop of conveyor is inside the irradiation chamber 2. A turntable 10 is in front of the scan horn 12. The revolving door 6 comprises two recesses 8 located 180° from each other. The diameter of the revolving door 6 is slightly larger than the thickness of the shielding wall 4. In order to improve shielding effect of the door, the concrete material is replaced by iron or lead bricks 14 in the areas where a thickness of concrete would not be sufficient, i.e. in the centre wall between the two recesses 8, and at the mouths of the recesses 8. A dual-recess revolving door 6 allows a good throughput of the apparatus, by using the following sequence:

an untreated product pallet is brought in the outside recess 8, while simultaneously, a treated product pallet is brought from the irradiation chamber 2 into the inside recess 8 (this step takes about 10 sec);
The door 6 is revolved 180° (this step takes about 30 sec);
The treated product pallet 9 is now brought out of the recess 8 now open to the outside, and the untreated product pallet 9 is brought inside the irradiation chamber 2.

In this way, the revolving door 6 is always symmetrically loaded. By using such an inner conveyor loop, the processing rate of the irradiation, and of the rate of transfer trough the revolving door 6 may be uncoupled, and the overall throughput of the apparatus may be increased.

Figure 5:
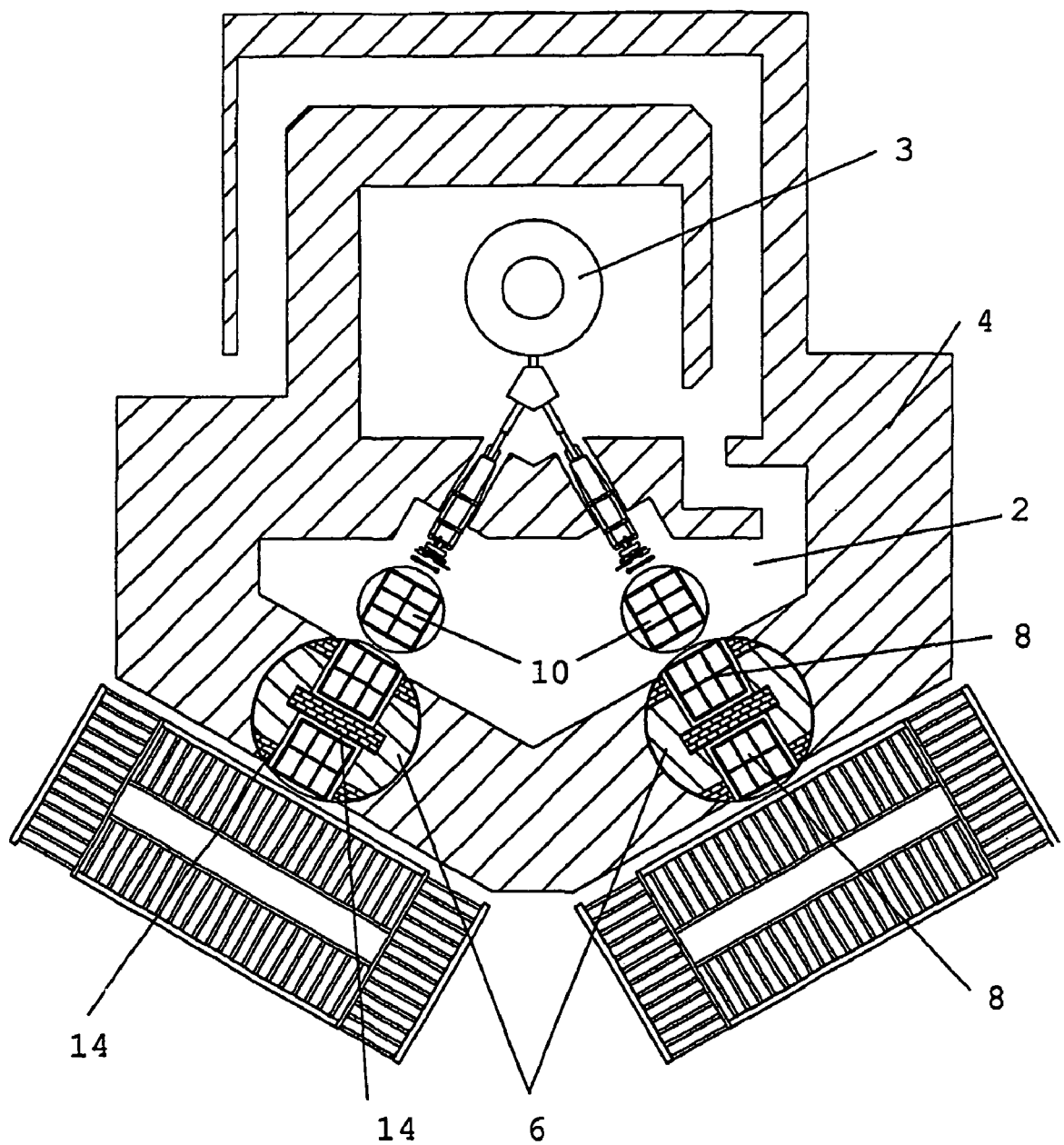
FIGS. 5, 6, 7 and 8 are different designs based on the first embodiment of the invention.
Figure 6:
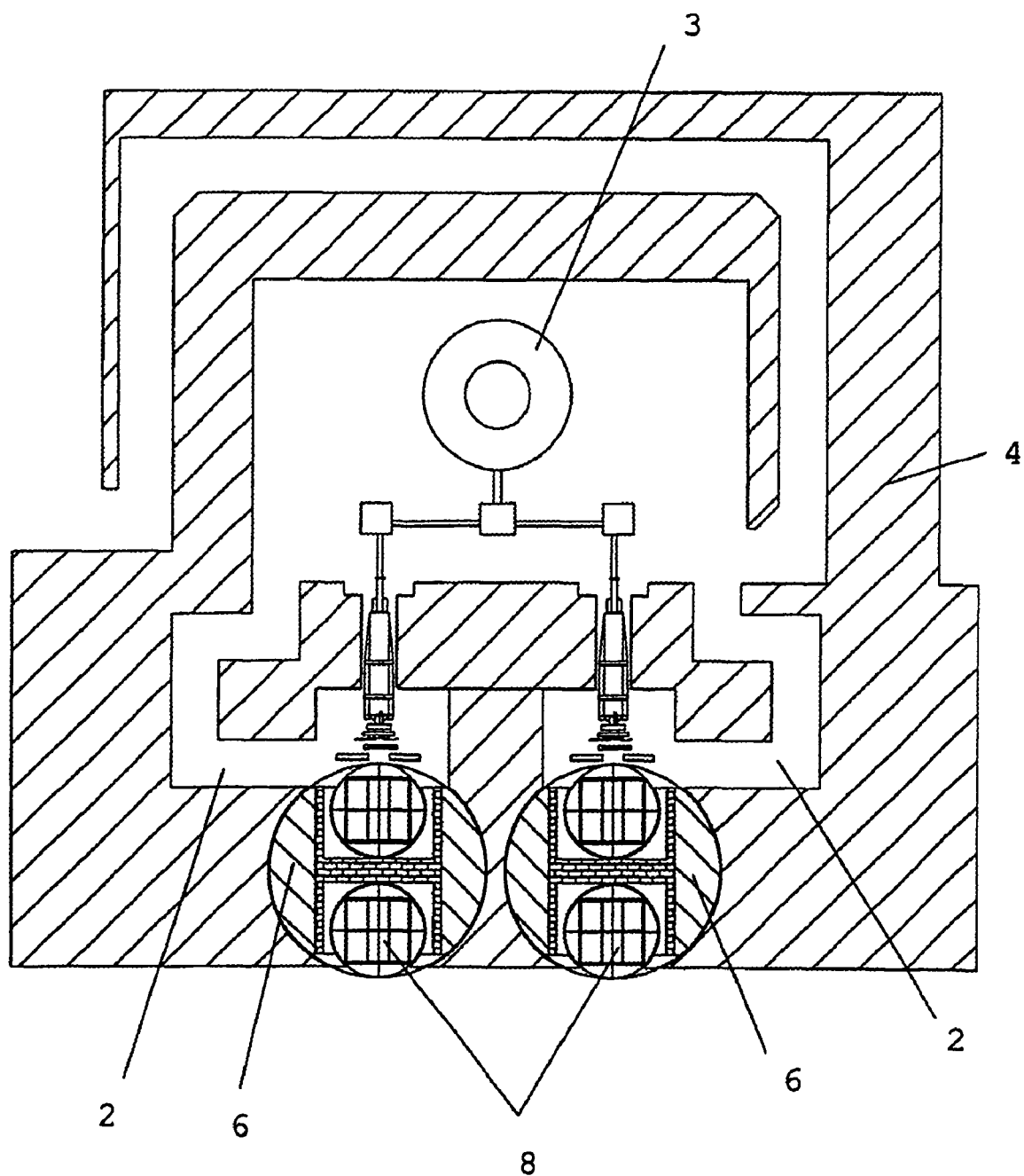

FIG. 5 shows a design having, like the design of FIG. 4, a dual recess revolving door. In addition, the apparatus comprises two revolving doors, two turntables, and two scan horns 12. A single radiation source 3 is directed to either of scan horns with a switching magnet. The "V" design of both beam lines allows a compact shielding and a small irradiation chamber 2. This design is shown here with turntables 10 inside the irradiation chamber 2, but may be modified according to the first embodiment, where said turntables 10 are inside the revolving door recesses 8. FIG. 6 shows a variation of this design, where the dual beam lines are parallel. The shielding wall 4 has a more conventional rectangular shape.

Figure 7:
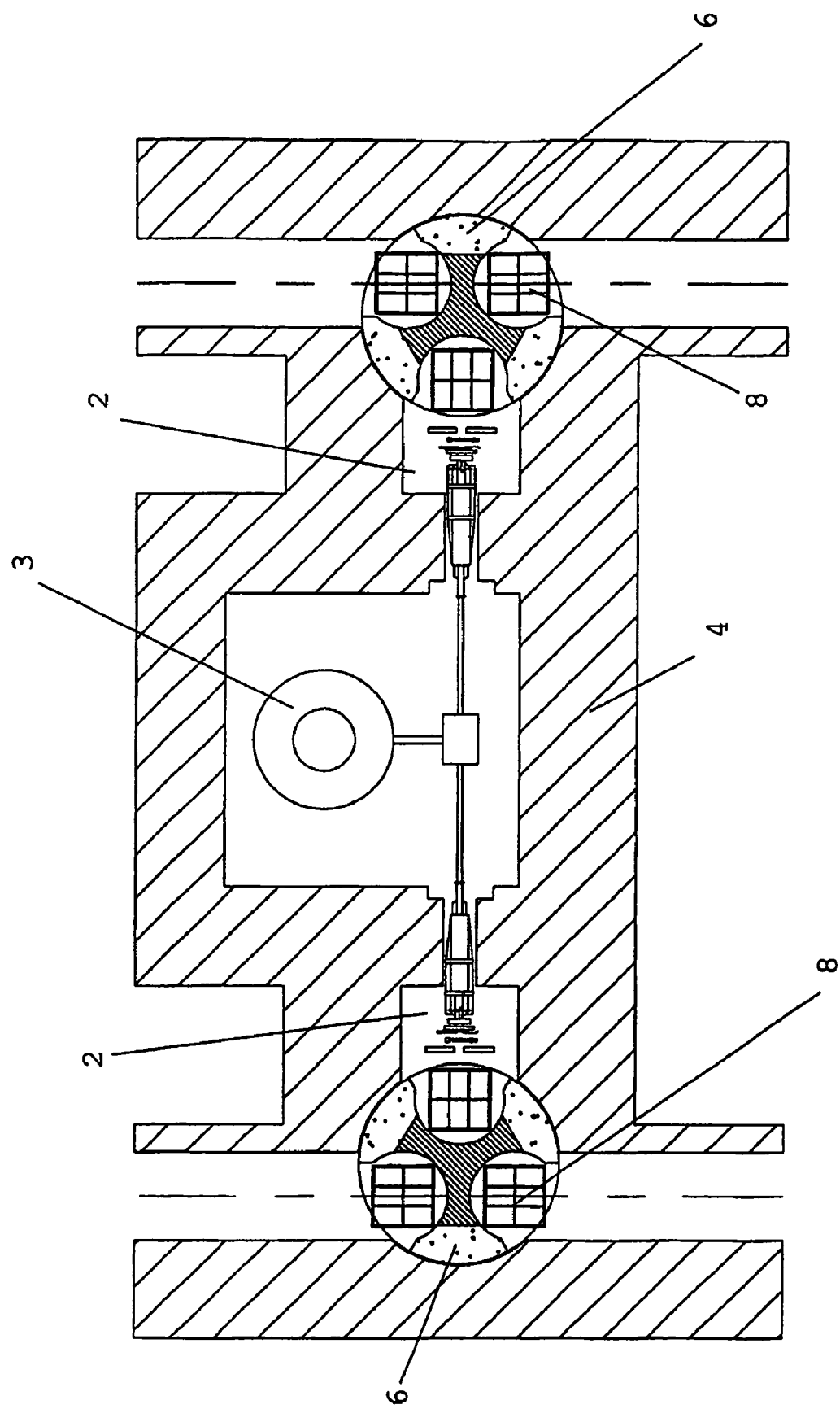
Figure 8:
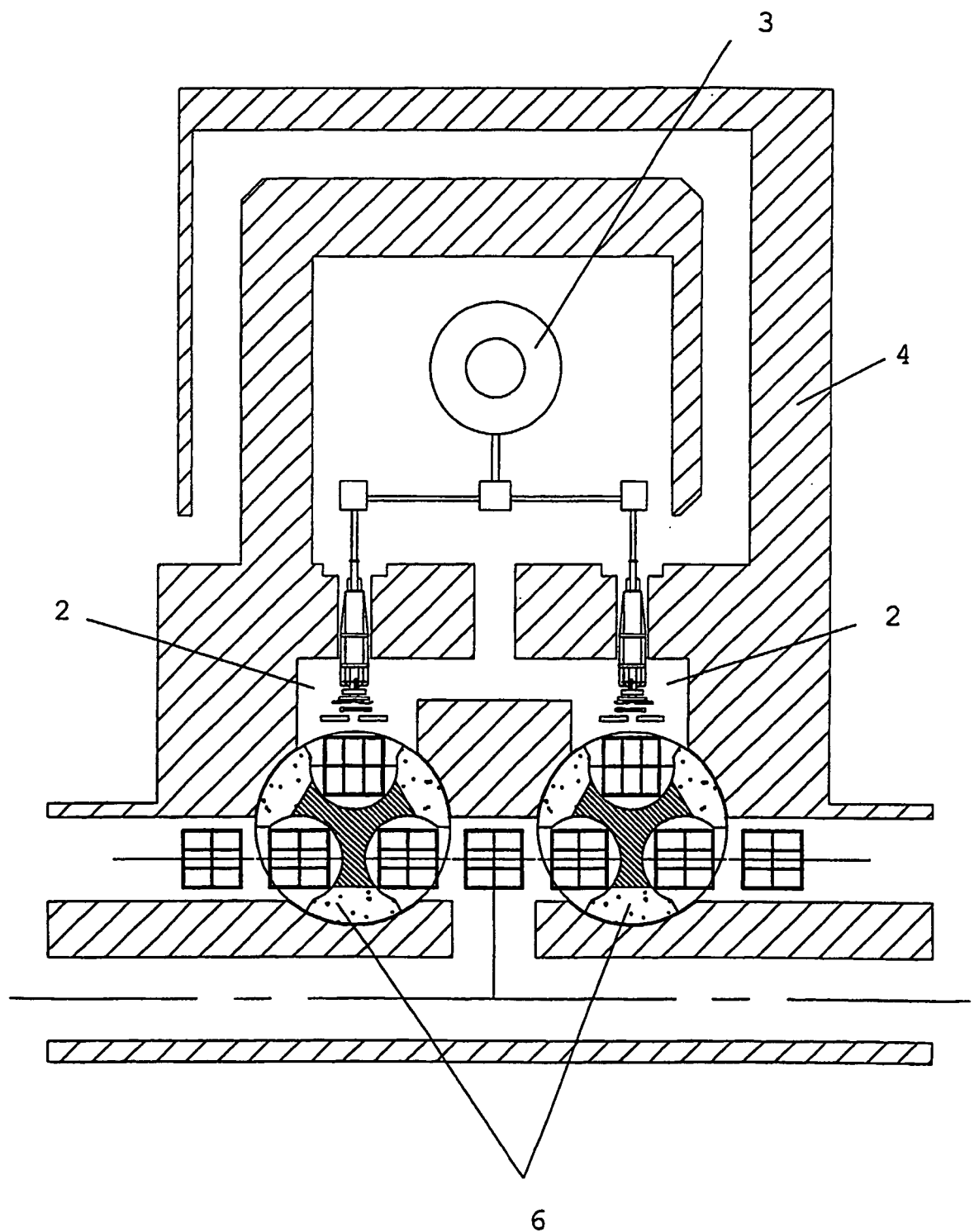

FIG. 7 and 8 are designs where the revolving doors 6 each have three recesses 8 spaced 120°. In the design of FIG. 7, the beam lines are directed in opposite directions by a single switching magnet. Two distinct conveyor paths are available. In the design of FIG. 8, the two lines share a common exit path.

Figure 9:
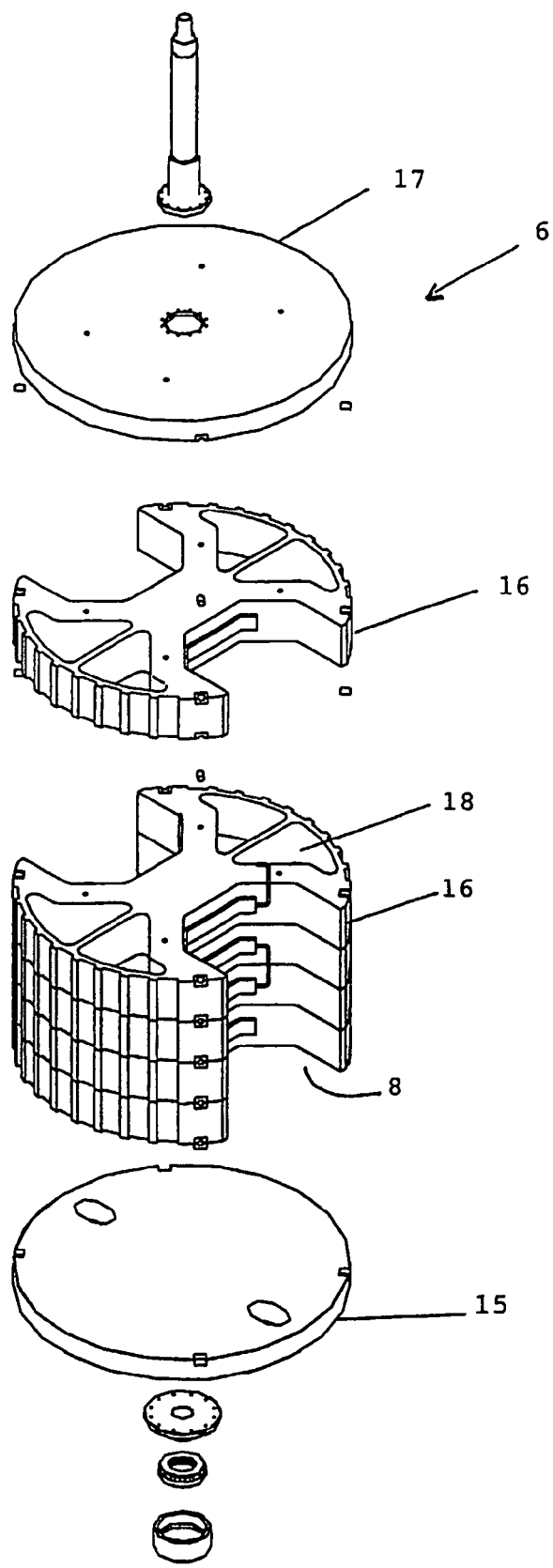
FIG. 9 is a perspective exploded view of a revolving door of an irradiation apparatus according to the present invention.

FIG. 9 shows a preferred construction of a revolving door 6 for an apparatus according to the invention. The overall weight of a revolving door 6 may be as high as 200 T. In order to make fabrication, transport and assembly easier, it is proposed to make the revolving door 6 with a base plate 15, a set of elements 16, and a top plate 17. The elements 16 have openings 18 which are filled with concrete after on-site assembly.

All embodiments of the invention and designs illustrated here above have a revolving door for bringing product pallets in and out of the irradiation chamber 2. This feature gives them a much more compact layout than the know maze designs. By using various combinations of multiple-recess doors, and multiple-door apparatuses, an optimal use of the irradiation source 3 can be achieved, thereby optimising throughput and/or minimizing transit time. The above designs must be considered as illustrative examples, not limiting the scope of the invention.

The invention claimed is:

1. An apparatus for sterilization of products conveyed on a pallet and for pasteurization of food products conveyed on a pallet, by irradiation, comprising:
   a beam source for producing a high-energy radiation beam;
   a shielding wall encompassing an irradiation chamber;
   a revolving door rotating about an axis and having at least one recess for holding said pallet, for bringing said pallet in and out of the irradiation chamber; and
   means for directing said high-energy radiation beam perpendicularly to the axis of rotation of said revolving door.

2. The apparatus of claim 1, wherein the apparatus comprises means for rotating said pallet during said irradiation.

3. The apparatus of claim 2, wherein said means for rotating comprise a turntable located inside said recess.

4. The apparatus of claim 1, wherein said means for rotating comprise a turntable located inside said irradiation chamber, the apparatus further comprising means for transferring said pallet outside of said recess, into said irradiation chamber, and onto said turntable for rotating said pallet.

5. The apparatus according to claim 1 further comprising two or more revolving doors, means for directing said high-energy radiation beam towards each revolving door in a horizontal direction, and means for switching said high energy radiation beam to each of said revolving doors.

6. The apparatus according to claim 1 wherein the revolving door comprises two or more recesses.

7. Process for sterilization of products conveyed on a pallet and for pasteurization of food products conveyed on a pallet, by irradiation, wherein the process comprises the steps of:
   revolving a cylindrical door for bringing a recess in said door to the outside of an irradiation chamber;
   transferring said pallet into said recess;
   revolving said cylindrical door about an axis for bringing said recess to the inside of said irradiation chamber;
   irradiating said product by directing a beam of high-energy radiation perpendicularly to the axis of rotation of said cylindrical door;
   revolving said cylindrical door for bringing said recess to the outside of said irradiation chamber;
   transferring said pallet out of said recess by a horizontal movement.

8. Process according to claim 7, further comprising the step of bringing said pallet out of said recess and into the irradiation chamber before irradiating it.

9. Process according to claim 7, further comprising the step of rotating said pallet during the irradiation.

10. Process according to claim 7, wherein a pallet is transferred in and/or out of a recess in a revolving door, while another pallet is being irradiated, placed in, or coming from another recess in said revolving door.

11. Process according to claim 7, wherein a pallet is being irradiated, placed in, or coming from a recess in a revolving door while another pallet is being transferred in and/or out of a recess in another revolving door and/or said other revolving door is being revolved.

* * * * *